US009968098B2

(12) United States Patent
Branscome et al.

(10) Patent No.: US 9,968,098 B2
(45) Date of Patent: May 15, 2018

(54) **SYNERGISTIC *BACILLUS THURINGIENSIS* SUBSP. *AIZAWAI, BACILLUS THURINGIENSIS* SUBSP. *KURSTAKI* AND CYANTRANILIPROLE MIXTURES FOR DIAMONDBACK MOTH, BEET ARMYWORM, SOUTHWESTERN CORN BORER, AND CORN EARWORM**

(71) Applicant: Valent BioSciences LLC, Libertyville, IL (US)

(72) Inventors: Deanna D. Branscome, Lake Villa, IL (US); Roger D. Storey, Hawthorn Woods, IL (US); James Russell Eldridge, Libertyville, IL (US); Emily E. Brazil, Gurnee, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days. days.

(21) Appl. No.: 15/498,647

(22) Filed: Apr. 27, 2017

(65) Prior Publication Data

US 2017/0311610 A1 Nov. 2, 2017

Related U.S. Application Data

(60) Provisional application No. 62/328,279, filed on Apr. 27, 2016.

(51) Int. Cl.
*A01N 63/00* (2006.01)
*A01N 43/56* (2006.01)

(52) U.S. Cl.
CPC ............. *A01N 63/00* (2013.01); *A01N 43/56* (2013.01)

(58) Field of Classification Search
CPC ...................................................... A01N 63/00
See application file for complete search history.

(56) References Cited

PUBLICATIONS

Riley (Journal of Entomological Science vol. 49(2), pp. 130-143) (Year: 2014).*

* cited by examiner

*Primary Examiner* — Albert M Navarro
*Assistant Examiner* — Mark Navarro
(74) *Attorney, Agent, or Firm* — Wood, Philips, Katz, Clark & Mortimer

(57) ABSTRACT

The present invention generally relates to the use of synergistic amounts of *Bacillus thuringiensis* subsp. *aizawai, Bacillus thuringiensis* subsp. *kurstaki* and cyantraniliprole for the control of diamondback moth, beet armyworm, southwestern corn borer, and corn earworm wherein the ratio of *Bacillus thuringiensis* subsp. *kurstaki* to *Bacillus thuringiensis* subsp. *aizawai* is from about 1:0.47 to about 1:0.92, and the ratio of the total amount of *Bacillus thuringiensis* to cyantraniliprole is from about 1:0.025 to about 1:150.

16 Claims, No Drawings

SYNERGISTIC *BACILLUS THURINGIENSIS* SUBSP. *AIZAWAI, BACILLUS THURINGIENSIS* SUBSP. *KURSTAKI* AND CYANTRANILIPROLE MIXTURES FOR DIAMONDBACK MOTH, BEET ARMYWORM, SOUTHWESTERN CORN BORER, AND CORN EARWORM

FIELD OF THE INVENTION

The present invention generally relates to the use of synergistic amounts of *Bacillus thuringiensis* subsp. *aizawai, Bacillus thuringiensis* subsp. *kurstaki* and cyantraniliprole for the control of diamondback moth, beet armyworm, southwestern corn borer, and corn earworm.

BACKGROUND OF THE INVENTION

Lepidoptera is an order of insects which includes moths and butterflies. It is estimated that there are over 174,000 Lepidopteran species, included in an estimated 126 families. Lepidopteran species undergo a complete metamorphosis during their life cycle. Adults mate and lay eggs. The larvae that emerge from the eggs have a cylindrical body and chewing mouth parts. Larvae undergo several growth stages called instars until they reach their terminal instar and then pupate. Lepidoptera then emerge as adult butterflies or moths.

While some Lepidoptera species are generally considered beneficial organisms due to their aesthetic appeal, many species cause devastating damage to crops. Specifically, diamondback moths, beet armyworms, southwestern corn borers, and corn earworm are especially problematic to crop growers.

Diamondback moths (*Plutella xylostella*) are a widespread pest that can disperse long distances. Diamondback moths and their larvae eat the leaves, buds, flowers and seed-buds of cruciferous plants. A heavy infestation can completely remove all foliar tissue from a plant leaving only the leaf veins. Even a lighter infestation can result in the unsuitability of an entire lot of produce for sale. In the past, diamondback moths have been treated with a variety of insecticides including pyrethroids and other insecticides.

Beet armyworms (*Spodoptera exigua*) are another widespread pest that is difficult to control. The larvae are voracious eaters that defoliate host plants. Older instars can also burrow into the plants. The damage to the host plant renders it unmarketable. Beet armyworms are pests on numerous types of crops.

Sugarcane borers (*Diatraea saccharalis*) mostly attack sugarcane and sweet corn crops, but will also infest other host plants. The larvae burrow into the stalks of the older plants causing the plant to weaken and break off or die. In younger plants, the inner whorl of leaves will die and yields will be impacted. Secondary fungal infections may also commonly occur as a result of seed cane predation. There has been some success in controlling sugarcane borers with insecticides but they need to be applied to the plants before the larvae burrow into the stalks.

Southwestern corn borers (*Diatraea grandiosella*) are a moth with a range extending from the southern United States to Central America. Southwestern corn borers are pest to highly consumed and profitable crops such as corn and sugarcane. The larvae feed within the whorl of the corn plant early in the life cycle of the plant often destroying the bud resulting in complete loss of yield.

Soybean loopers (*Chrysodeixis includens*) are a moth that is prevalent in North and South America. The larvae of soybean loopers can inflict heavy foliage damage resulting in significant crop loss. Soybean loopers are difficult to control with insecticides. Infestation of soybean loopers can be exacerbated after a non-selective insecticide removes the soybean loopers' natural predators.

Cabbage loopers (*Trichoplusia ni*) are are another widespread pest that can disperse long distances. Cabbage loopers eat leaves of many crops including cabbage, broccoli, cauliflower, turnip, rapeseed, mustard, radish horseradish, cress, wasabi, watercress, tomato, cucumber, collard greens and potato. Cabbage loopers are difficult to control and have displayed resistance to Dipel® (available from Valent BioSciences LLC, Dipel is a registered trademark of Valent BioSciences LLC). Janmaat, A F et al., Rapid evolution and the cost of resistance to *Bacillus thuringiensis* in greenhouse populations of cabbage loopers, *Trichoplusia ni., Proc Biol Sci.* 2003 Nov. 7, 270(1530), 2263-2270.

Corn earworms (*Helicoverpa zea*) have been referred to as the most costly crop pest in the United States. Corn earworms are difficult to control with insecticides because they can burrow into the plants and avoid exposure to insecticide applications. Corn earworms have numerous natural predators but predators and parasitoids alone are not effective at preventing crop plant damage by *Helicoverpa zea.*

*Bacillus thuringiensis* is a natural soil bacterium. Many *Bacillus thuringiensis* strains produce crystal proteins during sporulation called δ-endotoxins which can be used as biological insecticides. *Bacillus thuringiensis*, subspecies *aizawai* and *kurstaki*, produce crystals which paralyze the digestive system of some larvae within minutes. The larvae eventually die of starvation. *Bacillus thuringiensis* subsp. *aizawai* is commercially available as XenTari® (available from Valent BioSciences LLC, XenTari is a registered trademark of Valent BioSciences LLC). *Bacillus thuringiensis* subsp. *kurstaki* is commercially available as Dipel® (available from Valent BioSciences LLC, Dipel is a registered trademark of Valent BioSciences LLC).

One advantage of using *Bacillus thuringiensis* subsp. *aizawai* and *Bacillus thuringiensis* subsp. *kurstaki* is that they are target specific. They do not harm humans or other non-target species. Frequently when plants are treated with a non-selective insecticide, the insecticide also kills natural predators of other pests. This can cause a rebound effect in the target insect or other opportunistic pest species. For example, after applying a non-selective pesticide to kill borers, a spider mite infestation might occur because the non-selective pesticide also killed the spider mites' natural predators.

Yet another advantage of *Bacillus thuringiensis* subsp. *aizawai* and *Bacillus thuringiensis* subsp. *kurstaki* is that they can be used on organic crops. With no mandated pre-harvest interval, it can also be used on crops right before harvest. This provides organic growers, who have few options for pest control, a safe and effective way to manage insect infestations that could ultimately ruin an entire crop.

Cyantraniliprole (3-Bromo-1-(3-chloro-2-pyridinyl)-N-[4-cyano-2-methyl-6-(methylcarbamoyl)phenyl]-1H-pyrazole-5-carboxamide is an anthranilic diamide. Cyantraniliprole has low toxicity to humans and mammals. Further, it is effective at low use rates. Like *Bacillus thuringiensis*, cyantraniliprole is most effective when eaten by larvae. Cyantraniliprole forces muscles within the larvae to release all of their stored calcium, causing the larvae to stop eating and eventually die. Cyantraniliprole is commercially available, for example, as Exirel® (available from DuPont, Exirel is a registered trademark of E.I. du Pont de Nemours and Company).

Accordingly, there is a need for safe and effective ways to control diamondback moth, beet armyworm, southwestern corn borer, and corn earworm. These methods should be easy to apply, have increased efficacy, and be cost effective.

SUMMARY OF THE INVENTION

The present invention is directed to methods for controlling diamondback moth (*Plutella xylostella*), beet armyworm (*Spodoptera exigua*), southwestern corn borer (*Diatraea grandiosella*), and corn earworm (*Helicoverpa zea*) comprising applying a synergistic amount of *Bacillus thuringiensis* subsp. *aizawai, Bacillus thuringiensis* subsp. *kurstaki* and cyantraniliprole to a plant, wherein the weight ratio of *Bacillus thuringiensis* subsp. *kurstaki* to *Bacillus thuringiensis* subsp. *aizawai* is from about 1:0.47 to about 1:0.92, and the weight ratio of the total amount of *Bacillus thuringiensis* to cyantraniliprole is from about 1:0.025 to about 1:150.

DETAILED DESCRIPTION OF THE INVENTION

Applicant discovered that the use of *Bacillus thuringiensis* subsp. *aizawai, Bacillus thuringiensis* subsp. *kurstaki* and cyantraniliprole at a ratio range of from about 1:0.025 to about 1:150 provided unexpected synergistic effects against specific Lepidopteran species. This synergy was unexpected because the response to the treatment was highly species specific and unpredictable.

The *Bacillus thuringiensis* subsp. *aizawai, Bacillus thuringiensis* subsp. *kurstaki* and cyantraniliprole synergistic mixtures are safe to use on edible plants. Further, the components of the mixtures are target specific and pose low to no risk to beneficial insects or animals.

Another advantage of the present invention is that the combination of *Bacillus thuringiensis* subsp. *aizawai, Bacillus thuringiensis* subsp. *kurstaki* and cyantraniliprole aligns with Integrated Pest Management (IPM) principles and will reduce the ability of the insects to develop resistance to cyantraniliprole. By combining different products with different modes of action, the ability of the insects to dominantly express mutations which overcome both the *Bacillus thuringiensis* toxins and cyantraniliprole is very unlikely. A further advantage of the present invention is that having two types of *Bacillus thuringiensis* together exposes the larvae to a broader range of toxins. This means that the mixture of *Bacillus thuringiensis* subsp. *aizawai, Bacillus thuringiensis* subsp. *kurstaki* and cyantraniliprole can be applied repeatedly in the same season and year after year with minimal risk or resistance developing.

Yet another advantage of the present invention is that it allows for less *Bacillus thuringiensis* and less cyantraniliprole to be applied to the plant. For example, within label rates, sub-lethal doses of each can be applied to achieve a lethal dose and control of the larvae. This allows for a significant cost saving to the grower.

A further advantage is that *Bacillus thuringiensis* subsp. *aizawai, Bacillus thuringiensis* subsp. *kurstaki* and cyantraniliprole are target-specific. This means that humans and other, non-target organisms—such as natural predators of diamondback moth, sugarcane borer, soybean looper, and corn earworm—will not be harmed by the methods of the present invention.

In an embodiment, the present invention is directed methods for controlling a crop plant pest selected from the group consisting of diamondback moth (*Plutella xylostella*), beet armyworm (*Spodoptera exigua*), southwestern corn borer (*Diatraea grandiosella*), and corn earworm (*Helicoverpa zea*) comprising applying a synergistic amount of *Bacillus thuringiensis* subsp. *aizawai, Bacillus thuringiensis* subsp. *kurstaki* and cyantraniliprole to a plant, wherein the weight ratio of *Bacillus thuringiensis* subsp. *kurstaki* to *Bacillus thuringiensis* subsp. *aizawai* is from about 1:0.47 to about 1:0.92, and the weight ratio of the total amount of *Bacillus thuringiensis* to cyantraniliprole is from about 1:0.025 to about 1:150.

As used herein, "crop plant pest" only refers to diamondback moth (*Plutella xylostella*), beet armyworm (*Spodoptera exigua*), southwestern corn borer (*Diatraea grandiosella*), and corn earworm (*Helicoverpa zea*).

In a preferred embodiment, the weight ratio of *Bacillus thuringiensis* subsp. *kurstaki* to *Bacillus thuringiensis* subsp. *aizawai* is from about 1:0.53 to about 1:0.82. In a more preferred embodiment, the weight ratio of *Bacillus thuringiensis* subsp. *kurstaki* to *Bacillus thuringiensis* subsp. *aizawai* is about 1:0.67.

In a preferred embodiment, the weight ratio of the total amount of *Bacillus thuringiensis* to cyantraniliprole is from about 1:0.05 to about 1:60. In a more preferred embodiment, the weight ratio of the total amount of *Bacillus thuringiensis* to cyantraniliprole is from about 1:0.1 to about 1:26.

In another embodiment, the present invention is directed to methods for controlling a crop plant pest wherein the amount of *Bacillus thuringiensis* subsp. *aizawai/Bacillus thuringiensis* subsp. *kurstaki* is from about 5 to about 400 grams per hectare. In a preferred embodiment, the amount of *Bacillus thuringiensis* subsp. *aizawai/Bacillus thuringiensis* subsp. *kurstaki* is from about 10 to about 350 grams per hectare. In a more preferred embodiment, the amount of *Bacillus thuringiensis* subsp. *aizawai/Bacillus thuringiensis* subsp. *kurstaki* is from about 25 to about 300 grams per hectare.

In another embodiment, the present invention is directed to methods for controlling a crop plant pest wherein the amount of *Bacillus thuringiensis* subsp. *aizawai* is from about 2 to about 160 grams per hectare. In a preferred embodiment, the amount of *Bacillus thuringiensis* subsp. *aizawai* is from about 4 to about 140 grams per hectare. In a more preferred embodiment, the amount of *Bacillus thuringiensis* subsp. *aizawai* is from about 10 to about 120 grams per hectare.

In a further embodiment, the present invention is directed to methods for controlling a crop plant pest wherein the amount of *Bacillus thuringiensis* subsp. *kurstaki* is from about 3 to about 240 grams per hectare. In a preferred embodiment, the amount of *Bacillus thuringiensis* subsp. *kurstaki* is from about 6 to about 210 grams per hectare. In a more preferred embodiment, the amount of *Bacillus thuringiensis* subsp. *kurstaki* is from about 15 to about 180 grams per hectare.

In yet another embodiment, the present invention is directed to methods for controlling a crop plant pest wherein the total amount of *Bacillus thuringiensis* is from about 1,000 to about 100,000 *Spodoptera* U/mg. In a preferred embodiment, the amount of *Bacillus thuringiensis* is from about 10,000 to about 90,000 *Spodoptera* U/mg. In a more preferred embodiment, the amount of *Bacillus thuringiensis* is from about 15,000 to about 70,000 *Spodoptera* U/mg.

Although in some embodiments, the rates of *Bacillus thuringiensis* subsp. *aizawai* and *Bacillus thuringiensis* subsp. *kurstaki* are expressed in grams/hectare, IU/mg, or *Spodoptera* U/mg, the invention is not limited to these methods of measuring potency. If other products are developed or marketed with other potency measurements, it is within the knowledge of one of skill in the art, based on Applicant's teaching herein, to convert the rates to effective amounts consistent with the invention herein to achieve synergistic control of the target crop plant pest.

Further, the present invention is not limited to a specific type of formulation. For example, in the examples herein, an emulsifiable suspension was used as the source of *Bacillus thuringiensis* subsp. *aizawai/Bacillus thuringiensis kurstaki*. However, other types of formulations may be used, including but not limited to, wettable powder formulations, water dispersible granules, dry flowable granules, and other granules. Technical grade powders may also be used.

In yet another embodiment, the present invention is directed to methods for controlling a crop plant pest wherein the amount of cyantraniliprole is from about 10 to about 700 grams per hectare. In a preferred embodiment, the amount of cyantraniliprole is from about 25 to about 600 grams per hectare. In a more preferred embodiment, the amount of cyantraniliprole is from about 50 to about 525 grams per hectare.

Suitable *Bacillus thuringiensis* subsp. *aizawai* subspecies strains include, but are not limited to, VBTS-1857, GB413 and GC-91, and transconjugated, recombinant and/or genetically engineered subspecies thereof.

Suitable *Bacillus thuringiensis* subsp. *aizawai* commercial products include, but are not limited to, XenTari® (as indicated above, available from Valent BioSciences LLC, XenTari is a registered trademark of Valent BioSciences LLC), Solbit (available from Green Biotech Company), Bacchus® (available from Certis, Bacchus is registered trademark of Certis USA, L.L.C.), Agree® (available from Certis, Agree is registered trademark of Certis USA, L.L.C.), Jackpot® (available from Certis, Jackpot is registered trademark of Certis USA, L.L.C.), and Turex® (available from Certis, Turex is registered trademark of Certis USA, L.L.C.).

Suitable *Bacillus thuringiensis* subsp. *kurstaki* subspecies strains include, but are not limited to, VBTS-2546, BMP-123, EG-2348, EVB113-19, HD-1, PB-54, SA-11, SA-12, SB4, Z-52, EG-7841, ABTS-351, VBTS-2528, VBTS-2546, and transconjugated, recombinant and/or genetically engineered subspecies thereof.

Suitable *Bacillus thuringiensis* subsp. *kurstaki* commercial products include, but are not limited to, DiPel® (as indicated above, available from Valent BioSciences LLC, DiPel is a registered trademark of Valent BioSciences LLC), BMP 123 (available from Becker Microbials), Lepinox Plus (available from CBC Biogard), Rapax (available from CBC Biogard), Bioprotec 3P (available from AEF Global), *Bacillus* Chemia (available from Chemia), Biolarv (available from Agrimix), *Bacillus* Agrogen WP (available from Yaser Ltd), Merger/Belthirul (available from Probelte), Delfin® (available from Certis, Delfin is a registered trademark of Certis USA, L.L.C.), Javelin® WG (available from Certis, Javelin is a registered trademark of Certis USA, L.L.C.), Costar® (available from Certis, Costar is a registered trademark of Certis USA, L.L.C.), Deliver® (available from Certis, Deliver is a registered trademark of Certis USA, L.L.C.), BeTa Pro (available from BASF), Biolep (available from Biotech International Ltd), Full-Bac WDG (available from Becker Microbial), *Bacillus* MiPeru WP (available from Manejos Integrados Peru SA), and Crymax® (available from Certis, Crymax is a registered trademark of Certis USA, L.L.C.).

The examples herein used a commercial product of cyantraniliprole but the invention is not limited to the use of this commercial product. Suitable cyantraniliprole products include, but are not limited to, Exirel® (available from and a registered trademark of E.I. du Pont de Nemours and Company).

In a further embodiment, the present invention is directed to methods for controlling a crop plant pest comprising applying a synergistic amount of *Bacillus thuringiensis* subsp. *aizawai, Bacillus thuringiensis* subsp. *kurstaki* and cyantraniliprole wherein the ratio of *Bacillus thuringiensis* subsp. *aizawai* to *Bacillus thuringiensis* subsp. *kurstaki* is from 1:0.47 to about 1:0.92, and the ratio of the total amount of *Bacillus thuringiensis* to cyantraniliprole is from about 1:0.025 to about 1:150, and wherein the plant is selected from the group consisting of root, corm and tuber vegetables, bulb vegetables, leafy non-*brassica* vegetables, leafy *brassica* vegetables, succulent or dried legumes, fruiting vegetables, cucurbit vegetables, citrus fruits, pome fruits, stone fruits, berry and small fruits, tree nuts, cereal grains, forage and fodder grasses and hay, non-grass animal feeds, herbs, spices, flowers, bedding plants, ornamental flowers, artichoke, asparagus, coffee, cotton, tropical fruits, hops, malanga, peanut, pomegranate, oil seed vegetables, sugarcane, tobacco, turf, and watercress.

In another embodiment, the crop plant is genetically modified. A "genetically modified" crop plant is one that has had specific genes removed, modified or additional gene copies of native or foreign DNA. The change in the crop plant's DNA may result in can result in changes in the type or amount of RNA, proteins and/or other molecules that the crop plant produces which may affect its response to abiotic (e.g., herbicide) or biotic (e.g., insects) stresses, and/or affect its growth, development, or yield.

In a preferred embodiment, the root, corm and tuber vegetables are selected from the group consisting of arracacha, arrowroot, Chinese artichoke, Jerusalem artichoke, garden beet, sugar beet, edible burdock, edible *canna*, carrot, bitter cassava, sweet cassava, celeriac, root chayote, turnip-rooted chervil, chicory, chufa, dasheen (taro), ginger, *ginseng*, horseradish, leren, turnip-rooted parsley, parsnip, potato, radish, oriental radish, rutabaga, salsify, black salsify, Spanish salsify, skirret, sweet potato, tanier, turmeric, turnip, yam bean, true yam, and cultivars, varieties and hybrids thereof. In another preferred embodiment, the bulb vegetables are selected from the group consisting of fresh chive leaves, fresh Chinese chive leaves, bulb daylily, *elegans Hosta*, bulb *fritillaria, fritillaria* leaves, bulb garlic, great-headed bulb garlic, serpent bulb garlic, kurrat, lady's leek, leek, wild leek, bulb lily, Beltsville bunching onion, bulb onion, Chinese bulb onion, fresh onion, green onion, macrostem onion, pearl onion, potato bulb onion, potato bulb, tree onion tops, Welsh onion tops, bulb shallot, fresh shallot leaves, and cultivars, varieties and hybrids thereof.

In a further embodiment, the leafy non-*brassica* vegetables are selected from the group consisting of Chinese spinach Amaranth, leafy Amaranth, arugula (roquette), cardoon, celery, Chinese celery, celtuce, chervil, Chinese spinach, edible-leaved *chrysanthemum*, garland *chrysanthemum*, corn salad, garden cress, upland cress, dandelion, dandelion leaves, sorrels (dock), endive (escarole), Florence fennel, head lettuce, leaf lettuce, orach, parsley, garden purslane, winter purslane, radicchio (red chicory), rhubarb, spinach, New Zealand spinach, vine spinach, Swiss chard, Tampala, and cultivars, varieties and hybrids thereof In another embodiment, the leafy *brassica* vegetables are selected from the group consisting of broccoli, Chinese broccoli (gai lon), broccoli raab (rapini), Brussels sprouts, cabbage, Chinese cabbage (bok choy), Chinese napa cabbage, Chinese mustard cabbage (gai choy), cauliflower, cavalo broccoli, collards, kale, kohlrabi, mizuna, mustard greens, mustard spinach, rape greens, turnip greens and cultivars, varieties and hybrids thereof In yet another embodiment, the succulent or dried vegetable legumes are selected from the group consisting of *Lupinus* beans, *Phaseolus* beans, *Vigna* beans, broad beans (fava), chickpea (garbanzo), guar, jackbean, lablab bean, lentil, *Pisum* peas, pigeon pea, soybean, immature seed soybean, sword bean, peanut, and cultivars, varieties and hybrids thereof. In a preferred embodiment, the *Lupinus* beans include grain lupin, sweet lupin, white lupin, white sweet lupin, and hybrids thereof. In another preferred embodiment, the *Phaseolus* beans include field bean, kidney bean, lima bean, navy bean, pinto bean, runner bean, snap bean, tepary bean, wax bean, and hybrids thereof. In yet another preferred embodiment, the *Vigna* beans include adzuki bean, asparagus bean, blackeyed bean, catjang, Chinese longbean, cowpea, Crowder pea, moth bean, mung bean, rice bean, southern pea, urd bean, yardlong bean, and hybrids thereof. In another embodiment, the *Pisum* peas include dwarf pea, edible-podded pea, English pea, field pea, garden pea, green pea, snow pea, sugar snap pea, and hybrids thereof. In a preferred embodiment, the dried vegetable legume is soybean. In a more preferred embodiment, the dried vegetable legume is genetically modified soybean.

In a further embodiment, the fruiting vegetables are selected from the group consisting of bush tomato, cocona, currant tomato, garden huckleberry, goji berry, groundcherry, martynia, naranjilla, okra, pea eggplant, pepino, bell peppers, non-bell peppers, roselle, eggplant, scarlet eggplant, African eggplant, sunberry, tomatillo, tomato, tree tomato, and cultivars, varieties and hybrids thereof. In a preferred embodiment, the peppers include bell peppers, chili pepper, cooking pepper, pimento, sweet peppers, and hybrids thereof.

In an embodiment, the cucurbit vegetables are selected from the group consisting of Chayote, Chayote fruit, waxgourd (Chinese preserving melon), citron melon, cucumber, gherkin, edible gourds, *Momordica* species, muskmelons, pumpkins, summer squashes, winter squashes, watermelon, and cultivars, varieties and hybrids thereof. In a preferred embodiment, edible gourds include hyotan, cucuzza, hechima, Chinese okra, and hybrids thereof. In another preferred embodiment, the *Momordica* vegetables include balsam apple, balsam pear, bittermelon, Chinese cucumber, and hybrids thereof. In another preferred embodiment, the muskmelon include true cantaloupe, cantaloupe, casaba, crenshaw melon, golden pershaw melon, honeydew melon, honey balls, mango melon, Persian melon, pineapple melon, Santa Claus melon, snake melon, and hybrids thereof. In yet another preferred embodiment, the summer squash include crookneck squash, scallop squash, straightneck squash, vegetable marrow, zucchini, and hybrids thereof. In a further preferred embodiment, the winter squash includes butternut squash, calabaza, hubbard squash, acorn squash, spaghetti squash, and hybrids thereof.

In another embodiment, the citrus fruits are selected from the group consisting of limes, calamondin, citron, grapefruit, Japanese summer grapefruit, kumquat, lemons, Mediterranean mandarin, sour orange, sweet orange, pummel, Satsuma mandarin, tachibana orange, tangelo, mandarin tangerine, tangor, trifoliate orange, uniq fruit, and cultivars, varieties and hybrids thereof. In a preferred embodiment, the limes are selected from the group consisting of Australian desert lime, Australian finger lime, Australian round lime, Brown River finger lime, mount white lime, New Guinea wild lime, sweet lime, Russell River lime, Tahiti lime, and hybrids thereof.

In an embodiment, the pome fruits are selected from the group consisting of apple, azarole, crabapple, loquat, mayhaw, medlar, pear, Asian pear, quince, Chinese quince, Japanese quince, tejocote, and cultivars, varieties and hybrids thereof In another embodiment, the stone fruits are selected from the group consisting of apricot, sweet cherry, tart cherry, nectarine, peach, plum, Chicksaw plum, Damson plum, Japanese plum, plumcot, fresh prune, and cultivars, varieties and hybrids thereof.

In a further embodiment, the berries and small fruits are selected from the group consisting of Amur river grape, *aronia* berry, bayberry, bearberry, bilberry, blackberry, blueberry, lowbush blueberry, highbush blueberry, buffalo currant, buffaloberry, che, Chilean guava, chokecherry, cloudberry, cranberry, highbush cranberry, black currant, red currant, elderberry, European barberry, gooseberry, grape, edible honeysuckle, huckleberry, jostaberry, Juneberry (Saskatoon berry), lingonberry, maypop, mountain pepper berries, mulberry, muntries, native currant, partridgeberry, phalsa, pincherry, black raspberry, red raspberry, riberry, salal, schisandra berry, sea buckthorn, serviceberry, strawberry, wild raspberry, and cultivars, varieties and hybrids thereof. In a preferred embodiment, the blackberries include Andean blackberry, arctic blackberry, bingleberry, black satin berry, boysenberry, brombeere, California blackberry, Chesterberry, Cherokee blackberry, Cheyenne blackberry, common blackberry, coryberry, darrowberry, dewberry, Dirksen thornless berry, evergreen blackberry, Himalayaberry, hullberry, lavacaberry, loganberry, lowberry, Lucreliaberry, mammoth blackberry, marionberry, mora, mures deronce, nectarberry, Northern dewberry, olallieberry, Oregon evergreen berry, phenomenalberry, rangeberry, ravenberry, rossberry, Shawnee blackberry, Southern dewberry, tayberry, youngberry, zarzamora, and hybrids thereof.

In another embodiment, the tree nuts are selected from the group consisting of almond, beech nut, Brazil nut, Brazilian pine, bunya, butternut, bur oak, Cajou nut, candlenut, cashew, chestnut, chinquapin, coconut, coquito nut, dika nut, gingko, Guiana chestnut, hazelnut (filbert), heartnut, hickory nut, Japanese horse-chestnut, macadamia nut, mongongo nut, monkey-pot, monkey puzzule nut, Okari nut, Pachira nut, peach palm nut, pecan, Pili nut, pistachio, Sapucaia nut, tropical almond, black walnut, English walnut, yellowhorn, and cultivars, varieties and hybrids thereof.

In a further embodiment, the cereal grains are selected from the group consisting of barley, buckwheat, pearl millet, proso millet, oats, corn, field corn, sweet corn, seed corn, popcorn, rice, rye, sorghum (milo), sorghum species, grain sorghum, sudangrass (seed), teosinte, triticale, wheat, wild rice, and cultivars, varieties and hybrids thereof. In a preferred embodiment, the cereal grain is corn. In a more preferred embodiment, the cereal grain is genetically modified corn.

In yet another embodiment, the grass forage, fodder and hay are selected from the group consisting of grasses that are members of the Gramineae family except sugarcane and those species included in the cereal grains group, pasture and range grasses, and grasses grown for hay or silage. In further embodiments, the Gramineae grasses may be green or cured.

In an embodiment, the non-grass animal feeds are selected from the group consisting of alfalfa, velvet bean, *trifolium* clover, melilotus clover, kudzu, *lespedeza*, lupin, sainfoin, trefoil, vetch, crown vetch, milk vetch, and cultivars, varieties and hybrids thereof.

In another embodiment, the herbs and spices are selected from the group consisting of allspice, *angelica*, anise, anise seed, star anise, annatto seed, balm, basil, borage, burnet, chamomile, caper buds, caraway, black caraway, cardamom, *cassia* bark, *cassia* buds, catnip, celery seed, chervil, chive, Chinese chive, cinnamon, clary, clove buds, coriander leaf, coriander seed, costmary, culantro leaves, culantro seed, cilantro leaves, cilantro seed, cumin, dillweed, dill seed, fennel, common fennel, Florence fennel seed, fenugreek, grains of paradise, horehound, hyssop, juniper berry, lavender, lemongrass, leaf lovage, seed lovage, mace, marigold, marjoram, mint, mustard seed, nasturtium, nutmeg, parsley, pennyroyal, black pepper, white pepper, poppy seed, rosemary, rue, saffron, sage, summer savory, winter savory, sweet bay, tansy, tarragon, thyme, vanilla, wintergreen, woodruff, wormwood, and cultivars, varieties and hybrids thereof. In a preferred embodiment, the mints are selected from the group consisting of spearmint, peppermint, and hybrids thereof.

In yet another embodiment, artichokes are selected from the group consisting of Chinese artichoke, Jerusalem artichoke, and cultivars, varieties and hybrids thereof.

In an embodiment, the tropical fruits are selected from the group consisting of anonna, avocado, fuzzy kiwifruit, hardy kiwifruit, banana, plantain, caimito, carambola (star fruit), guava, longan, sapodilla, *papaya*, passion fruit, mango, lychee, jackfruit, dragon fruit, mamey sapote, coconut cherimoya, canistrel, monster, wax jambu, pomegranate, rambutan, pulasan, Pakistani mulberry, langsat, chempedak, durian, fig pineapple, jaboticaba, mountain apples, pineapple, and cultivars, varieties and hybrids thereof.

In a further embodiment, the oil seed vegetables are selected from the group consisting of borage, calendula, castor oil plant, tallowtree, cottonseed, *crambe, cuphea*, echium, *euphorbia*, evening primrose, flax seed, gold of pleasure, hare's ear, mustard, jojoba, *lesquerella*, lunaria, meadowfoam, milkweed, niger seed, oil radish, poppy seed, rosehip, sesame, stokes aster, sweet rocket, tallowwood, tea oil plant, vermonia, canola, or oil rapeseed, safflower, sunflower, and cultivars, varieties and hybrids thereof.

The synergistic amounts of *Bacillus thuringiensis* subsp. *aizawai, Bacillus thuringiensis* subsp. *kurstaki* and cyantraniliprole may be applied to seeds, foliage, or an area where a plant is intended to grow.

The synergistic amounts of *Bacillus thuringiensis* subsp. *aizawai, Bacillus thuringiensis* subsp. *kurstaki* and cyantraniliprole may be applied once or many times during a growing season. If *Bacillus thuringiensis* subsp. *aizawai, Bacillus thuringiensis* subsp. *kurstaki* and cyantraniliprole are applied more than one time, the total amount applied should not exceed a yearly maximum rate as determined by environmental protection agencies or relevant label rates.

As used herein, "plant" refers to at least one plant and not a plant population.

As used herein, "control" or "controlling" means a decline in the amount of damage to the plants from the larvae, reduction of pest population, interference with life cycle development or other physiological or behavioral effect that results in plant protection.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The disclosed embodiments are simply exemplary embodiments of the inventive concepts disclosed herein and should not be considered as limiting, unless so stated.

The following examples are intended to illustrate the present invention and to teach one of ordinary skill in the art how to make and use the invention. They are not intended to be limiting in any way.

EXAMPLES

The following examples were used to determine the synergy of *Bacillus thuringiensis* subsp. *aizawai, Bacillus thuringiensis* subsp. *kurstaki* and cyantraniliprole when controlling diamondback moth, beet armyworm, sugarcane borer, soybean looper, corn earworm, cabbage looper, and southwestern corn borer. Sympatico™ emulsifiable suspension (available from Valent BioSciences LLC) was used as the source of *Bacillus thuringiensis* subsp. *aizawai* and *Bacillus thuringiensis kurstaki*. Sympatico™ contains about a 1:0.67 ratio of *Bacillus thuringiensis* subsp. *kurstaki* fermentation solids, spores and toxins to *Bacillus thuringiensis* subsp. *aizawai* fermentation solids, spores and toxins. Belt® was used as the source of cyantraniliprole. The present invention is not limited to the commercial products used in the examples. In each example below, the studies were conducted as follows.

For these tests, standardized laboratory leaf dip methods were used to inoculate plant material with treatment(s). Dry, treated leaves were placed into Petri dishes (100×25 mm) containing filter paper wetted with 500 µl of distilled $H_2O$ ("d$H_2O$"). Each dish was then infested with between 5 and 10 larvae, dependent on species. Efficacy ratings were taken at specified intervals. Synergy ratings were calculated for each test.

Example 1—Diamondback Moth

In this study, the response of diamondback moth larvae to synergistic amounts of *Bacillus thuringiensis* subsp. *aizawai* ("Bta"), *Bacillus thuringiensis* subsp. *kurstaki* ("Btk") and cyantraniliprole was observed. The results of this study can be seen below in Table 1.

TABLE 1

| Time after treatment (h) | % Efficacy Neg. Control d$H_2O$ | Bta/Btk | Cyantraniliprole | Bta/Btk + cyantraniliprole (Ratio 1:0.12) | Synergy Ratio |
|---|---|---|---|---|---|
| 24 | 2 | 2 | 29 | 37 | 1.19 |
| 48 | 3 | 11 | 52 | 59 | No Synergy |

As seen in Table 1, the mixtures of the present invention provided a more than additive effect. By using the following formula, Applicant was able to determine that this response was synergistic: % $C_{exp}$=A+B−(AB/100).

% $C_{exp}$=A+B−(AB/100), where % $C_{exp}$ is the expected efficacy and "in which A and B are the control levels given by the single [insecticides]. If the ratio between the experimentally observed efficacy of the mixture $C_{obs}$ and the expected efficacy of the mixture is greater than 1, synergistic interactions are present in the mixture." (Gisi, *Synergisitic*

*Interaction of Fungicides in Mixtures*, The American Phytopathological Society, 86:11, 1273-1279, 1996). Adopting a conservative approach, Applicant will determine if synergy is present at ratios of ≥1.15.

*Bacillus thuringiensis* subsp. *aizawai/Bacillus thuringiensis* subsp. *kurstaki* was applied at a concentration of 0.8125 ppm (0.8125 μg/ml). Cyantraniliprole was applied at a concentration of 0.12 ppm (0.12 μg/ml). The *Bacillus thuringiensis* subsp. *aizawai/Bacillus thuringiensis kurstaki*/cyantraniliprole mixture was applied at a concentration of 0.8125 ppm *Bacillus thuringiensis* subsp. *aizawai/Bacillus thuringiensis* subsp. *kurstaki* and 0.12 ppm cyantraniliprole.

In order to determine synergy, rates below normal field rate ranges must be used. If normal field rate ranges are used, all of the larvae would die (combining a lethal or near lethal dose of *Bacillus thuringiensis* subsp. *aizawai* and *Bacillus thuringiensis* subsp. *kurstaki* with a lethal dose of cyantraniliprole would most likely lead to larvae death) in every treatment and synergy would not be able to be determined. A synergy ratio that is indicative of synergy is this assay is a predictor of the synergy that will be seen in the field at normal field rates (or at rates that occur naturally as the active ingredients are degraded over time by exposure to rain, UV radiation, and temperature extremes). This assay was chosen for its ability to accurately predict mortality rates of larvae in the field.

The results of this calculation indicated that the synergy ratio was 1.19 at 24 hours. As a finding of higher than 1 is indicative of synergy (per Gisi, or even ≥1.15 per Applicant), the ratios of 1.19 is synergistic. Synergy was shown at a ratio of *Bacillus thuringiensis* subsp. *aizawai/Bacillus thuringiensis* subsp. *kurstaki* to cyantraniliprole of 1:0.12.

Example 2—Beet Armyworm

In this study, the response of beet armyworm larvae to synergistic amounts of *Bacillus thuringiensis* subsp. *aizawai, Bacillus thuringiensis* subsp. *kurstaki* and cyantraniliprole was observed. The results of this study can be seen below in Table 2.

TABLE 2

| Time | % Efficacy | | | | |
|---|---|---|---|---|---|
| after treatment (h) | Neg. Control $dH_2O$ | Bta/Btk | Cyantraniliprole | Bta/Btk + cyantraniliprole (Ratio 1:1.23) | Synergy Ratio |
| 24 | 0 | 1 | 20 | 29 | 1.38 |
| 48 | 0 | 1 | 35 | 41 | 1.16 |

*Bacillus thuringiensis* subsp. *aizawai/Bacillus thuringiensis* subsp. *kurstaki* was applied at a concentration of 0.8125 ppm (0.8125 μg/ml). Cyantraniliprole was applied at a concentration of 1.0 ppm (1.0 μg/ml). The *Bacillus thuringiensis* subsp. *aizawai/Bacillus thuringiensis kurstaki*/cyantraniliprole mixture was applied at a concentration of 0.8125 ppm *Bacillus thuringiensis* subsp. *aizawai/Bacillus thuringiensis* subsp. *kurstaki* and 1.0 ppm cyantraniliprole.

As seen in Table 2, the mixtures of the present invention provided a more than additive effect. By using the following formula, Applicant was able to determine that this response was synergistic: % $C_{exp}$=A+B−(AB/100).

The results of this calculation indicated that the synergy ratio was 1.38 at 24 hours and 1.16 at 48 hours. As a finding of higher than 1 is indicative of synergy (per Gisi, or even ≥1.15 per Applicant), the ratios of 1.38 and 1.16 are synergistic. Synergy was shown at a ratio of *Bacillus thuringiensis* subsp. *aizawai/Bacillus thuringiensis* subsp. *kurstaki* to cyantraniliprole of 1:1.23.

Example 3—Cabbage Looper

In this study, the response of cabbage looper larvae to amounts of *Bacillus thuringiensis* subsp. *aizawai, Bacillus thuringiensis* subsp. *kurstaki* and cyantraniliprole was observed. The results of this study can be seen below in Table 3.

TABLE 3

| Time | % Efficacy | | | | |
|---|---|---|---|---|---|
| after treatment (h) | Neg. Control $dH_2O$ | Bta/Btk | Cyantraniliprole | Bta/Btk + cyantraniliprole (Ratio 1:0.62) | Synergy Ratio |
| 24 | 1 | 0 | 18 | 15 | No Synergy |
| 48 | 1 | 1 | 40 | 33 | No Synergy |

*Bacillus thuringiensis* subsp. *aizawai/Bacillus thuringiensis* subsp. *kurstaki* was applied at a concentration of 0.8125 ppm (0.8125 μg/ml). Cyantraniliprole was applied at a concentration of 0.50 ppm (0.50 μg/ml). The *Bacillus thuringiensis* subsp. *aizawai/Bacillus thuringiensis kurstaki*/cyantraniliprole mixture was applied at a concentration of 0.8125 ppm *Bacillus thuringiensis* subsp. *aizawai/Bacillus thuringiensis* subsp. *kurstaki* and 0.50 ppm cyantraniliprole.

As seen in Table 3, the mixtures of the present invention did not provide a more than additive effect. By using the following formula, Applicant was able to determine that this response was not synergistic: % $C_{exp}$=A+B−(AB/100).

Example 4—Sugarcane Borer

In this study, the response of sugarcane borer larvae to *Bacillus thuringiensis* subsp. *aizawai, Bacillus thuringiensis* subsp. *kurstaki* and cyantraniliprole was observed. The results of this study can be seen below in Table 4.

TABLE 4

| Time | % Efficacy | | | | |
|---|---|---|---|---|---|
| after treatment (h) | Neg. Control $dH_2O$ | Bta/Btk | Cyantraniliprole | Bta/Btk + cyantraniliprole (Ratio 1:1.23) | Synergy Ratio |
| 24 | 1 | 2 | 24 | 23 | No Synergy |
| 48 | 2 | 6 | 35 | 34 | No Synergy |

*Bacillus thuringiensis* subsp. *aizawai/Bacillus thuringiensis* subsp. *kurstaki* was applied at a concentration of 0.8125 ppm (0.8125 μg/ml). Cyantraniliprole was applied at a concentration of 1.0 ppm (2.15 μg/ml). The *Bacillus thuringiensis* subsp. *aizawai/Bacillus thuringiensis kurstaki*/cyantraniliprole mixture was applied at a concentration of 0.8125 ppm *Bacillus thuringiensis* subsp. *aizawai/Bacillus thuringiensis* subsp. *kurstaki* and 1.0 ppm cyantraniliprole.

As seen in Table 4, the mixtures of the present invention did not provide more than an additive effect. By using the following formula, Applicant was able to determine that this response was not synergistic: % $C_{exp}$=A+B−(AB/100).

Example 5—Southwestern Corn Borer

In this study, the response of southwestern corn borer larvae to synergistic amounts of *Bacillus thuringiensis* subsp. *aizawai, Bacillus thuringiensis* subsp. *kurstaki* and cyantraniliprole was observed. The results of this study can be seen below in Table 5.

TABLE 5

| Time after treatment (h) | % Efficacy Neg. Control $dH_2O$ | Bta/Btk | Cyantraniliprole | Bta/Btk + cyantraniliprole (Ratio 1:0.12) | Synergy Ratio |
|---|---|---|---|---|---|
| 24 | 2 | 3 | 15 | 18 | No Synergy |
| 48 | 4 | 8 | 32 | 46 | 1.23 |

*Bacillus thuringiensis* subsp. *aizawai/Bacillus thuringiensis* subsp. *kurstaki* was applied at a concentration of 0.8125 ppm (0.8125 μg/ml). Cyantraniliprole was applied at a concentration of 0.1 ppm (0.1 μg/ml). The *Bacillus thuringiensis* subsp. *aizawai/Bacillus thuringiensis kurstaki*/ cyantraniliprole mixture was applied at a concentration of 0.8125 ppm *Bacillus thuringiensis* subsp. *aizawai/Bacillus thuringiensis* subsp. *kurstaki* and 0.1 ppm cyantraniliprole.

As seen in Table 5, the mixtures of the present invention provided a more than additive effect. By using the following formula, Applicant was able to determine that this response was synergistic: % $C_{exp}$=A+B−(AB/100).

The results of this calculation indicated that the synergy ratio was 1.23 at 48 hours. As a finding of higher than 1 is indicative of synergy (per Gisi, or even ≥1.15 per Applicant), the ratios of 1.23 is synergistic. Synergy was shown at a ratio of *Bacillus thuringiensis* subsp. *aizawai/Bacillus thuringiensis* subsp. *kurstaki* to cyantraniliprole of 1:0.12.

Example 6—Soybean Looper

In this study, the response of soybean looper larvae to *Bacillus thuringiensis* subsp. *aizawai, Bacillus thuringiensis* subsp. *kurstaki* and cyantraniliprole was observed. The results of this study can be seen below in Table 6.

TABLE 6

| Time after treatment (h) | % Efficacy Neg. Control $dH_2O$ | Bta/Btk | Cyantraniliprole | Bta/Btk + cyantraniliprole (Ratio 1:15) | Synergy Ratio |
|---|---|---|---|---|---|
| 24 | 0 | 0 | 12 | 5 | No Synergy |
| 48 | 0 | 1 | 41 | 29 | No Synergy |

*Bacillus thuringiensis* subsp. *aizawai/Bacillus thuringiensis* subsp. *kurstaki* was applied at a concentration of 0.26 ppm (0.26 μg/ml). Cyantraniliprole was applied at a concentration of 1.0 ppm (1.0 μg/ml). The *Bacillus thuringiensis* subsp. *aizawai/Bacillus thuringiensis kurstaki*/cyantraniliprole mixture was applied at a concentration of 0.26 ppm *Bacillus thuringiensis* subsp. *aizawai/Bacillus thuringiensis* subsp. *kurstaki* and 1.0 ppm cyantraniliprole.

As seen in Table 6, the mixtures of the present invention did not provide a more than additive effect. By using the following formula, Applicant was able to determine that this response was synergistic: % $C_{exp}$=A+B−(AB/100).

Example 7—Corn Earworm

In this study, the response of corn earworm larvae to amounts of *Bacillus thuringiensis* subsp. *aizawai, Bacillus thuringiensis* subsp. *kurstaki* and cyantraniliprole was observed. The results of this study can be seen below in Table 7.

TABLE 7

| Time after treatment (h) | % Efficacy Neg. Control $dH_2O$ | Bta/Btk | Cyantraniliprole | Bta/Btk + cyantraniliprole (Ratio 1:3.85) | Synergy Ratio |
|---|---|---|---|---|---|
| 24 | 0 | 0 | 44 | 53 | 1.21 |
| 48 | 4 | 24 | 60 | 63 | No Synergy |

*Bacillus thuringiensis* subsp. *aizawai/Bacillus thuringiensis* subsp. *kurstaki* was applied at a concentration of 2.6 ppm (2.6 μg/ml). Cyantraniliprole was applied at a concentration of 10.0 ppm (10.0 μg/ml). The *Bacillus thuringiensis* subsp. *aizawai/Bacillus thuringiensis kurstaki*/cyantraniliprole mixture was applied at a concentration of 2.6 ppm *Bacillus thuringiensis* subsp. *kurstaki/Bacillus thuringiensis* subsp. *aizawai* and 10.0 ppm cyantraniliprole.

As seen in Table 7, the mixtures of the present invention provided a more than additive effect. By using the following formula, Applicant was able to determine that this response was synergistic: % $C_{exp}$=A+B−(AB/100).

The results of this calculation indicated that the synergy ratio was 1.21 at 24 hours. As a finding of higher than 1 is indicative of synergy (per Gisi, or even ≥1.15 per Applicant), the ratio of 1.21 is synergistic. Synergy was shown at a ratio of *Bacillus thuringiensis* subsp. *aizawai/Bacillus thuringiensis* subsp. *kurstaki* to cyantraniliprole of 1:3.85.

We claim:

1. A method of controlling a crop plant pest selected from the group consisting of Diamondback moth (*Plutella xylostella*), Beet armyworm (*Spodoptera exigua*), Southwestern corn borers (*Diatraea grandiosella*), and Corn earworm (*Helicoverpa zea*) comprising applying a synergistic amount of *Bacillus thuringiensis* subsp. *aizawai, Bacillus thuringiensis* subsp. *kurstaki* and cyantraniliprole to a plant, wherein the ratio of *Bacillus thuringiensis* subsp. *kurstaki* to *Bacillus thuringiensis* subsp. *aizawai* is from about 1:0.47 to about 1:0.92, and the ratio of the total amount of *Bacillus thuringiensis* to cyantraniliprole is from about 1:0.025 to about 1:150.

2. The method of claim 1 wherein the ratio of *Bacillus thuringiensis* subsp. *kurstaki* to *Bacillus thuringiensis* subsp. *aizawai* is from about 1:0.53 to about 1:0.82.

3. The method of claim 1 wherein the ratio of the total amount of *Bacillus thuringiensis* to cyantraniliprole is from about 1:0.05 to about 1:60.

4. The method of claim 1 wherein the amount of *Bacillus thuringiensis* subsp. *aizawai* is from about 2 to about 160 grams per hectare.

5. The method of claim 1 wherein the amount of *Bacillus thuringiensis* subsp. *kurstaki* is from about 3 to about 240 grams per hectare.

6. The method of claim 1 wherein the amount of cyantraniliprole is from about 10 to about 700 grams per hectare.

7. The method of claim 1 wherein the crop plant pest is Diamondback moth (*Plutella xylostella*).

8. The method of claim 1 wherein the crop plant pest is Beet armyworm (*Spodoptera exigua*).

9. The method of claim 1 wherein the crop plant pest is Southwestern corn borers (*Diatraea grandiosella*).

10. The method of claim 1 wherein the crop plant pest is Corn earworm (*Helicoverpa zea*).

11. The method of claim 1 wherein the plant is selected from the group consisting of root, corm and tuber vegetables, bulb vegetables, leafy non-*brassica* vegetables, leafy *brassica* vegetables, succulent or dried legumes, fruiting vegetables, cucurbit vegetables, citrus fruits, pome fruits, stone fruits, berry and small fruits, tree nuts, cereal grains, forage and fodder grasses and hay, non-grass animal feeds, herbs, spices, flowers, bedding plants, ornamental flowers, artichoke, asparagus, coffee, cotton, tropical fruits, hops, malanga, peanut, pomegranate, oil seed vegetables, sugarcane, tobacco, turf, and watercress.

12. The method of claim 11 wherein the plant is genetically modified.

13. The method of claim 11 wherein the cereal grains are selected from the group consisting of barley, buckwheat, pearl millet, proso millet, oats, corn, field corn, sweet corn, seed corn, popcorn, rice, rye, sorghum (milo), sorghum species, grain sorghum, sudangrass (seed), teosinte, triticale, wheat, wild rice, and cultivars, varieties and hybrids thereof.

14. The method of claim 13 wherein the plant is genetically modified corn.

15. The method of claim 11 wherein the succulent or dried vegetable legumes are selected from the group consisting of *Lupinus* beans, *Phaseolus* beans, *Vigna* beans, broad beans, chickpea, guar, jackbean, lablab bean, lentil, *Pisum* peas, pigeon pea, soybean, immature seed soybean, sword bean, peanut, and cultivars, varieties and hybrids thereof.

16. The method of claim 15 wherein the plant is genetically modified soybean.

* * * * *